(12) United States Patent
Yakura et al.

(10) Patent No.: US 10,743,784 B2
(45) Date of Patent: Aug. 18, 2020

(54) ACTION MANAGEMENT APPARATUS, ACTION MANAGEMENT METHOD, AND ACTION MANAGEMENT PROGRAM

(71) Applicant: OMRON HEALTHCARE CO., LTD., Muko-shi, Kyoto (JP)

(72) Inventors: Nobuki Yakura, Kyoto (JP); Takehiro Hamaguchi, Kyoto (JP); Mitsuru Samejima, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 307 days.

(21) Appl. No.: 15/614,071

(22) Filed: Jun. 5, 2017

(65) Prior Publication Data

US 2017/0269933 A1    Sep. 21, 2017

Related U.S. Application Data

(63) Continuation of application No. PCT/JP2015/082531, filed on Nov. 19, 2015.

(30) Foreign Application Priority Data

Dec. 4, 2014    (JP) ................... 2014-245929

(51) Int. Cl.
*A61B 5/024*    (2006.01)
*A61B 5/11*    (2006.01)
(Continued)

(52) U.S. Cl.
CPC ........ *A61B 5/02438* (2013.01); *A61B 5/1118* (2013.01); *A61B 5/1122* (2013.01);
(Continued)

(58) Field of Classification Search
CPC .. G06F 9/30021; A61B 5/1122; A61B 5/1118; A61B 5/222; A61B 5/721; A61B 5/02438; A61B 2503/20; G06K 9/0053
See application file for complete search history.

(56) References Cited

U.S. PATENT DOCUMENTS

| | | | |
|---|---|---|---|
| 2005/0200487 A1 | 9/2005 | O'Donnell et al. | |
| 2007/0049462 A1* | 3/2007 | Asukai .................. | A63B 71/06 482/8 |

(Continued)

FOREIGN PATENT DOCUMENTS

| | | |
|---|---|---|
| CN | 1921317 A | 2/2007 |
| CN | 103520897 A | 1/2014 |

(Continued)

OTHER PUBLICATIONS

Definition of deviation in English, Lexico.com (powered by Oxford's English Dictionary), https://www.lexico.com/en/definition/deviation, viewed on Jun. 21, 2019.*

(Continued)

*Primary Examiner* — Christopher Koharski
*Assistant Examiner* — James Moss
(74) *Attorney, Agent, or Firm* — Oliff PLC

(57) ABSTRACT

An action management apparatus includes a bodily information measurement unit that measures bodily information, a communication unit for performing near-field wireless communication with another apparatus having a function of measuring bodily information, a bodily information acquisition unit that acquires the bodily information measured by the other apparatus included in a group along with the action management apparatus via a communication unit, and an information output unit that, based on first bodily information measured by the bodily information measurement unit and second bodily information acquired by the bodily information acquisition unit, outputs management information (Continued)

for managing an action of a wearer of an apparatus belonging to the group.

5 Claims, 6 Drawing Sheets

(51) Int. Cl.
*A61B 5/00* (2006.01)
*A61B 5/22* (2006.01)
*G06F 9/30* (2018.01)
*G06K 9/00* (2006.01)

(52) U.S. Cl.
CPC .............. *A61B 5/222* (2013.01); *A61B 5/721* (2013.01); *G06F 9/30021* (2013.01); *G06K 9/0053* (2013.01); *A61B 2503/20* (2013.01)

(56) References Cited

U.S. PATENT DOCUMENTS

| | | | |
|---|---|---|---|
| 2012/0116719 A1* | 5/2012 | Takahashi | A61B 5/1112 702/160 |
| 2012/0179007 A1* | 7/2012 | Rinehart | G06F 19/3468 600/301 |
| 2012/0254934 A1* | 10/2012 | McBrearty | G06F 19/3481 725/118 |
| 2015/0081062 A1 | 3/2015 | Fyfe et al. | |
| 2016/0080838 A1 | 3/2016 | Kim et al. | |
| 2016/0150039 A1 | 5/2016 | Miettinen et al. | |

FOREIGN PATENT DOCUMENTS

| | | |
|---|---|---|
| JP | 2003-242584 A | 8/2003 |
| JP | 2007-054450 A | 3/2007 |
| JP | 2008-503268 A | 2/2008 |
| JP | 2009-039157 A | 2/2009 |
| JP | 2011-090426 A | 5/2011 |
| JP | 2012-524638 A | 10/2012 |
| JP | 2012-213630 A | 11/2012 |
| JP | 2013-085895 A | 5/2013 |
| WO | 2016/027684 A1 | 2/2016 |

OTHER PUBLICATIONS

MathIsFun, "Percentage Change", https://web.archive.org/web/20140214111926/https://www.mathsisfun.com/numbers/percentage-change.html, Feb. 14, 2014, viewed on Jan. 9, 2019.*
GSMRENA, https://www.gsmarena.com/samsung_galaxy_s5-6033.php, viewed on Jan. 9, 2019.*
Sascha Segan, "Hands on with the Samsung Galaxy S5", https://www.pcmag.com/article/320958/hands-on-with-the-samsung-galaxy-s5, PC Mag, Feb. 14, 2014, viewed on Jan. 9, 2014.*
Feb. 23, 2016 International Search Report issued in International Patent Application No. PCT/JP2015/082531.
Nov. 1, 2019 Office Action Issued in U.S. Appl. No. 15/693,819.
May 28, 2019 Office Action issued in Chinese Patent Application No. 201580062687.4.
Apr. 12, 2016 International Search Report issued in Patent Application No. PCT/JP2016/056875.
Jul. 12, 2019 Office Action issued in U.S. Appl. No. 15/693,819.
U.S. Appl. No. 15/693,819, filed Sep. 1, 2017 in the name of Samejima.

* cited by examiner

ACTION MANAGEMENT APPARATUS, ACTION MANAGEMENT METHOD, AND ACTION MANAGEMENT PROGRAM

TECHNICAL FIELD

The present invention relates to an action management apparatus, an action management method, and an action management program.

BACKGROUND ART

In recent years, there have been many developments in exercise information measurement apparatuses that can measure exercise information such as an activity amount (step count, walking distance, expended calories, and the like) or a movement pace for exercise (walking speed, running speed, and the like) by using a motion detection sensor that detects motion of a body, such as an acceleration sensor or an angular velocity sensor.

There are known to be such exercise information measurement apparatuses that have a function of measuring bodily information indicating an exercise load, such as a pulse rate, a heart rate, or oxygen saturation, and various services can be provided by using this function.

For example, Patent Literature 1 discloses a system in which a server acquires bodily information from multiple exercise information measurement apparatuses, determines danger states of wearers of the exercise information measurement apparatuses, and transmits danger information to the exercise information measurement apparatuses worn by the wearers other than the wearer determined as being in a danger state.

Also, Patent Literature 2 discloses an exercise information measurement apparatus according to which it is possible to check, on a display unit, a status of a wearer of the exercise information measurement apparatus obtained based on bodily information measured by the exercise information measurement apparatus, and a status of a wearer of another apparatus obtained based on bodily information received from the other apparatus.

CITATION LIST

Patent Literature

Patent Literature 1: JP 2013-085895A
Patent Literature 2: JP 2009-039157A

SUMMARY OF INVENTION

Technical Problem

With the technique disclosed in Patent Literature 1, notification is performed if the bodily information of an individual reaches a dangerous level. Also, with the technique disclosed in Patent Literature 2, the state of the body of an individual can be kept track of visually.

However, in the case of performing an action in a group, for example, there are cases where knowing the state of the group as a whole is more important than knowing the state of the body of an individual.

For example, it can be said that if the pulse rates of all members of a group is slightly smaller than a dangerous level but none of the members of the group have a pulse rate that has reached the dangerous level, there is a high likelihood that there will be a member who reaches the dangerous level in the future, and therefore it is preferable to lower the exercise load for the entire group. However, with the techniques disclosed in Patent Literature 1 and 2, it is not possible to determine how to act as a group in such a case.

Also, in the case of performing an action in a group, there are cases where it is preferable to make a determination by comparing the state of a certain person belonging to the group with the states of the bodies of all of the members of the group.

For example, if the pulse rates of all of the members belonging to the group gradually increase and the pulse rate of a certain member rises faster than the other members even though none of the members have a pulse rate that has reached the dangerous level, it is possible to determine that an excessive load is being placed on the body of that user. For this reason, a measure such as causing that member to take a break is needed.

However, with the technique disclosed in Patent Literature 1 and 2, it is only possible to determine the state of the body of an individual using the bodily information of that individual, and therefore it is not possible to know that such a measure is needed in the case of performing a group action.

The present invention has been made in view of the foregoing circumstance and it is an object thereof to provide an action management apparatus, an action management method, and an action management program according to which it is possible to suitably manage a group action.

Solution to the Problem

An action management apparatus according to the present invention includes: a bodily information measurement unit configured to measure bodily information; a communication unit for performing near-field wireless communication with another apparatus having a function of measuring bodily information; a bodily information acquisition unit configured to, via the communication unit, acquire bodily information measured by another apparatus included in a group along with the action management apparatus; and an information output unit configured to, based on first bodily information measured by the bodily information measurement unit and second bodily information acquired by the bodily information acquisition unit, output management information for managing an action of a wearer of an apparatus belonging to the group.

An action management method according to the present invention is an action management method performed by an action management apparatus including a bodily information measurement unit configured to measure bodily information, and a communication unit for performing near-field wireless communication with another apparatus having a function of measuring bodily information, the method including: a bodily information acquisition step of, via the communication unit, acquiring bodily information measured by another apparatus included in a group along with the action management apparatus; and an information output step of, based on first bodily information measured by the bodily information measurement unit and second bodily information acquired in the bodily information acquisition step, outputting management information for managing an action of a wearer of an apparatus belonging to the group.

An action management program according to the present invention is a program for causing a computer to execute the steps of the action management method.

Advantageous Effects of Invention

According to the present invention, it is possible to provide an action management apparatus, an action management method, and an action management program according to which it is possible to suitably manage a group action.

DESCRIPTION OF EMBODIMENTS

Figure 1:
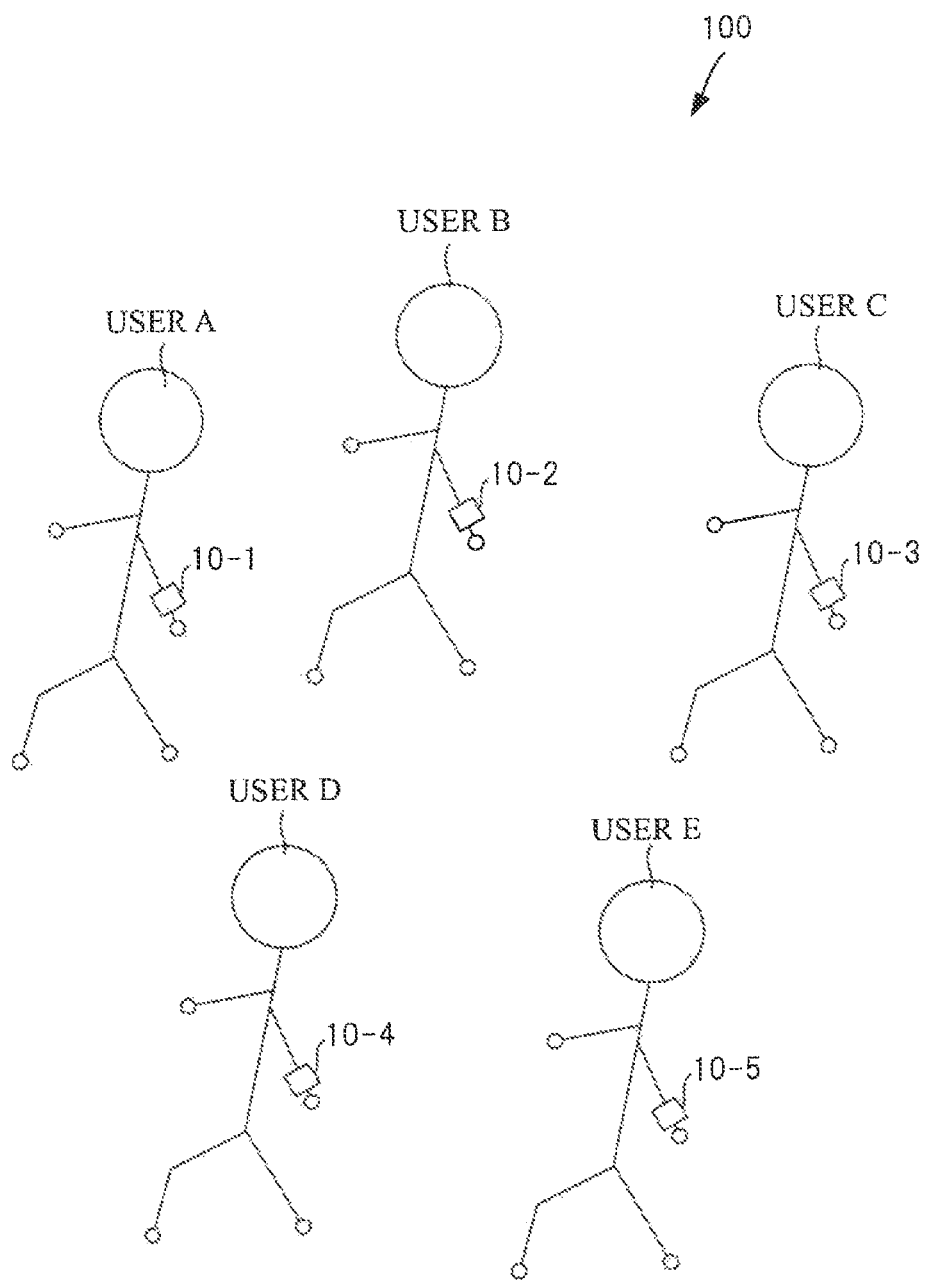
FIG. 1 is a diagram showing a schematic configuration of a system 100 for illustrating an embodiment of the present invention.

Hereinafter, embodiments of the present invention will be described with reference to the drawings. Note that in the following description and the accompanying drawings, constituent elements with approximately the same functional configurations are denoted by the same reference numerals, and redundant description thereof is not included.

FIG. 1 is a diagram showing a schematic configuration of a system 100 for illustrating an embodiment of the present invention. The system 100 includes exercise information measurement apparatuses 10-1 to 10-5 serving as multiple (in the example shown in FIG. 1, five) action management apparatuses. The exercise information measurement apparatuses 10-1 to 10-5 are used while worn on the bodies of users, and are pedometers, activity meters, sports watches, or the like, to be specific.

The exercise information measurement apparatuses 10-1 to 10-5 are each given identification information (ID). The ID of the exercise information measurement apparatus 10-1 is "01", the ID of the exercise information measurement apparatus 10-2 is "02", the ID of the exercise information measurement apparatus 10-3 is "03", the ID of the exercise information measurement apparatus 10-4 is "04", and the ID of the exercise information measurement apparatus 10-5 is "05".

In the present embodiment, a case is envisioned in which a group of five people, namely users A to E, perform mountain climbing. In this case, user A, user B, . . . , and user E respectively wear the exercise information measurement apparatuses 10-1, 10-2, . . . , and 10-5. Also, one of the users A to E is set as a leader of the group, and the leader manages the action of the group.

Note that in order to facilitate understanding of the description, it is assumed that user A (e.g., a teacher) is the group leader. The exercise information measurement apparatus 10-1 worn by user A is set in advance as a master device through an operation performed by user A. Also, the exercise information measurement apparatuses 10-2 to 10-5 worn by users B to E (e.g., students) are set as slave devices through operations performed by the users. Accordingly, user A (the teacher) can manage the action of the group that includes user A and the members (the students).

Hereinafter, if it is not necessary to distinguish between the individual exercise information measurement apparatuses 10-1 to 10-5, the expression "exercise information measurement apparatus 10" will be used.

Figure 2:
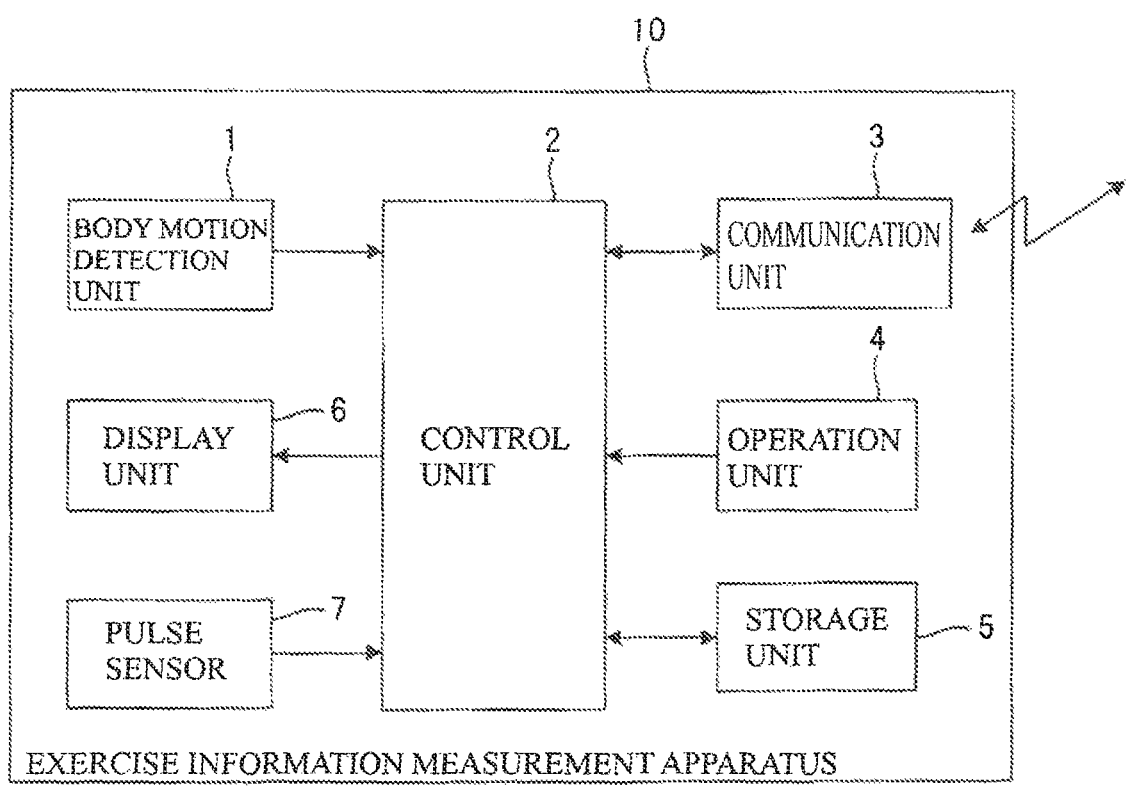
FIG. 2 is a block diagram showing an internal configuration of an exercise information measurement apparatus 10.

FIG. 2 is a block diagram showing an internal configuration of an exercise information measurement apparatus 10.

The exercise information measurement apparatus 10 includes a body motion detection unit 1, a control unit 2 that performs overall control, a communication unit 3, an operation unit 4, a storage unit 5 that includes a storage medium such as a flash memory or a ROM (Read Only Memory), a display unit 6 for displaying various types of information, and a pulse sensor 7.

The body motion detection unit 1 detects information (acceleration, angular velocity, and the like) corresponding to motion of a part of the body of a user to which the exercise information measurement apparatus 10 is attached (also includes a state in which the exercise information measurement apparatus 10 has been inserted in a pocket of a piece of clothing). The body motion detection unit 1 includes various sensors such as an acceleration sensor, an angular velocity sensor, and a geomagnetic sensor, and a signal processing unit that processes signals output from the various sensors. It is sufficient that the body motion detection unit 1 includes at least one motion sensor and a signal processing unit that processes signals from the motion sensor.

The control unit 2 is mainly constituted by a processor that executes a program stored in the ROM of the storage unit 5.

The communication unit 3 is an interface for performing near-field wireless communication with an electronic device including another exercise information measurement apparatus 10 (hereinafter referred to as "other device 10"). Near-field wireless communication refers to communication that conforms to a communication standard according to which direct communication can be performed between apparatuses without using a network such as the Internet. A communication interface that conforms to ANT, a communication interface that conforms to Bluetooth (registered trademark), or the like can be used as this interface.

The operation unit 4 is a device for inputting various instructions to the control unit 2, and is constituted by buttons, a touch panel mounted on a display unit 6, and the like.

The storage unit 5 stores detection information detected by the body motion detection unit 1, stores information received via the communication unit 3, and stores information needed for the operation of the exercise information measurement apparatus 10. The age of the wearer is registered in advance in the storage unit 5 by the wearer of the apparatus.

The pulse sensor 7 is a known sensor that detects a pulse.

Figure 3:
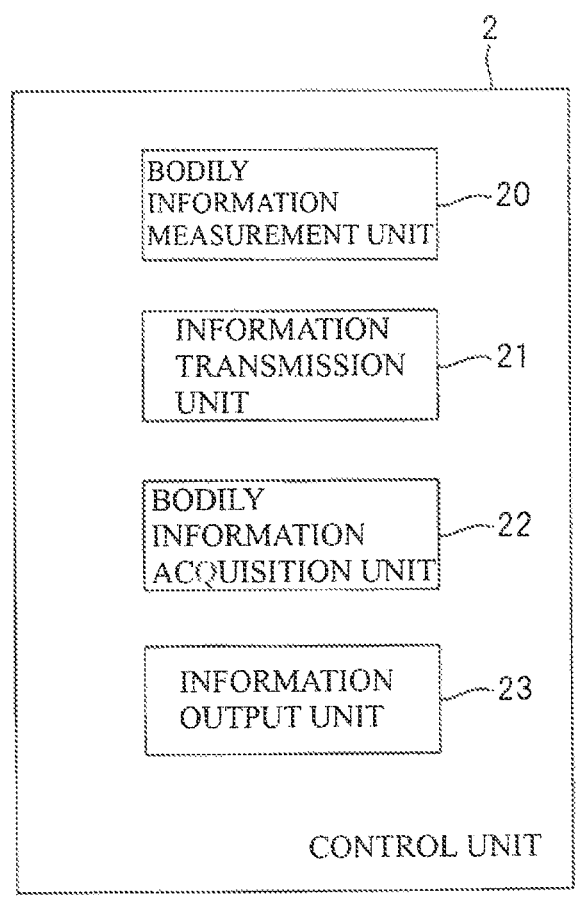
FIG. 3 is a diagram showing functional blocks realized by a control unit 2 due to a processor executing a program stored in a storage unit 5 of the exercise information measurement apparatus 10 of FIG. 2.

FIG. 3 is a diagram showing functional blocks realized by the control unit 2 due to a processor executing a program stored in the storage unit 5 of the exercise information measurement apparatus 10 shown in FIG. 2.

As shown in FIG. 3, the control unit 2 includes a bodily information measurement unit 20, an information transmission unit 21, a bodily information acquisition unit 22, and an information output unit 23.

Based on the detection signal of the pulse sensor 7, the bodily information measurement unit 20 measures the pulse rate, which is bodily information of the wearer of the apparatus, and the measured pulse rate is stored in the storage unit 5 in association with the ID of the apparatus and the maximum pulse rate of the wearer of the apparatus.

The information transmission unit 21 causes the pulse rate measured by the bodily information measurement unit 20, the ID of the apparatus, and the maximum pulse rate of the wearer of the apparatus to be transmitted from the communication unit 3 to the exercise information measurement apparatus 10 set as the master device. The information transmission unit 21 functions only in the case where the apparatus has been set as a slave device.

Note that the control unit 2 calculates the maximum pulse rate of the wearer by substituting the age of the wearer registered in the storage unit 5 into the commonly-known equation "maximum pulse rate=220−age".

The bodily information acquisition unit 22 acquires the ID of the apparatus, the pulse rate, and the maximum pulse rate that were transmitted from another apparatus 10 set as a slave device and were received by the communication unit 3, and the bodily information acquisition unit 22 stores the ID, the pulse rate, and the maximum pulse rate that were acquired in association with each other in the storage unit 5.

Accordingly, for the respective IDs of the exercise information measurement apparatuses 10-1 to 10-5, information on the pulse rates and the maximum pulse rates of the wearers of the apparatuses, which were measured by the bodily information measurement units 20 of the apparatuses, are stored in the storage unit 5 of the exercise information measurement apparatus 10 set as the master device.

Based on the respective pulse rates of the apparatus and the other apparatuses 10 stored in the storage unit 5, the information output unit 23 outputs management information for managing the actions of the wearers of the apparatuses belonging to the group that includes the apparatus and the other apparatuses 10. The information output unit 23 functions in the case where the apparatus is set as the master device. The management information is information according to which it is possible to determine whether or not an action of some or all group members is to be changed. As will be described below, examples of management information include information indicating the size of the exercise load of the entire group.

Operations performed by the system 100 constituted as described above will be described.

Figure 4:
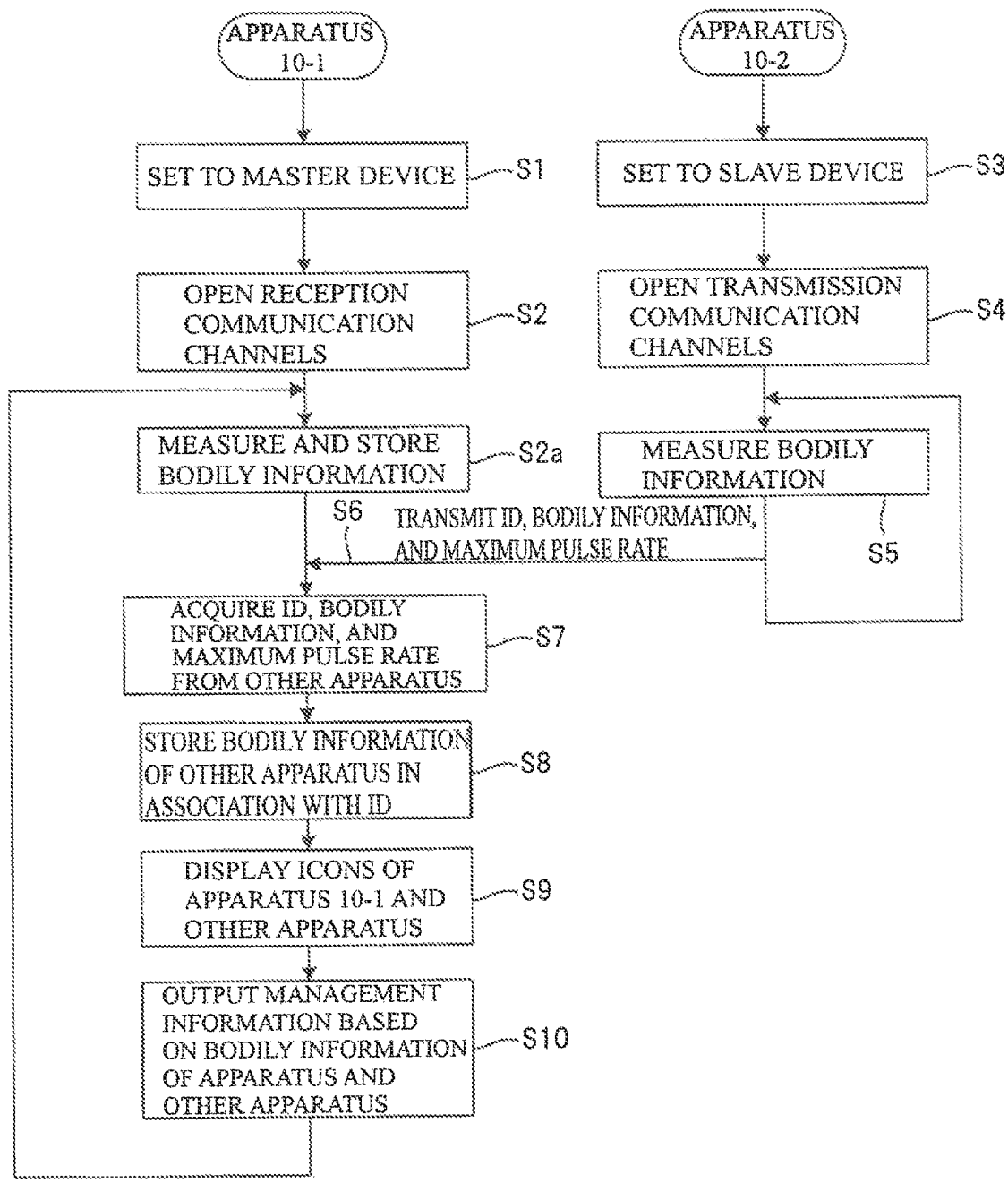
FIG. 4 is a flowchart for illustrating operations performed by the exercise information measurement apparatus 10 in the system 100.

FIG. 4 is a flowchart for illustrating operations performed by the exercise information measurement apparatus 10 in the system 100. FIG. 4 shows operations performed by the exercise information measurement apparatus 10-1 serving as the master device and one slave device (hereinafter assumed to be the exercise information measurement apparatus 10-2), and the operations shown in FIG. 4 are performed by the operation information measurement apparatus 10-1 and each slave device.

First, the group members (users A to E) who are to perform mountain climbing put on the exercise information measurement apparatuses 10-1 to 10-5. When the operation unit 4 of the exercise information measurement apparatus 10-1 worn by user A is operated by user A to perform a master device setting instruction, the control unit 2 of the exercise information measurement apparatus 10-1 sets the exercise information measurement apparatus 10-1 to be a master device (step S1).

When the setting of the master device is performed, the control unit 2 of the exercise information measurement apparatus 10-1 opens all of the reception communication channels of the communication unit 3 (step S2) and enters a state of waiting to receive information from a slave device.

After step S2, the bodily information measurement unit 20 of the exercise information measurement apparatus 10-1 starts measuring the pulse rate, and the measured pulse rate and the maximum pulse rate of the wearer of the exercise information measurement apparatus 10-1 are stored in the storage unit 5 in association with the ID of the exercise information measurement apparatus 10-1 (step S2a).

On the other hand, when users B to E operate the operation units 4 of the exercise information measurement apparatuses 10-2 to 10-5 to give slave device setting instructions, the control units 2 of the exercise information measurement apparatuses 10-2 to 10-5 set the respective apparatuses to be slave devices (step S3).

When the slave devices are set, the control units 2 of the exercise information measurement apparatuses 10 that are slave devices open the transmission communication channels of the communication units 3 (step S4) and transition to a state in which it is possible to communicate with another exercise information measurement apparatus 10. After step S4, the control units 2 of the exercise information measurement apparatuses 10 that are the slave devices start measuring the pulse rates (step S5).

In this state, if the exercise information measurement apparatus 10-2 is in a range in which communication with the communication unit 3 of the exercise information measurement apparatus 10-1 is possible, the pulse rate measured by the bodily information measurement unit 20 of the exercise information measurement apparatus 10-2, the ID of the exercise information measurement apparatus 10-2, and the maximum pulse rate of the wearer of the exercise information measurement apparatus 10-2 are transmitted to the exercise information measurement apparatus 10-1 and received by the exercise information measurement apparatus 10-1 (step S6).

When the exercise information measurement apparatus 10-2 is within the range in which communication with the communication unit 3 of the exercise information measurement apparatus 10-1 is possible, the exercise information measurement apparatus 10-2 periodically transmits the pulse rate measured by the bodily information measurement unit 20, the maximum pulse rate of the wearer, and the ID of the exercise information measurement apparatus 10-2 to the exercise information measurement apparatus 10-1.

In the exercise information measurement apparatus 10-1, the control unit 2 acquires the pulse rate, the maximum pulse rate, and the ID received by the communication unit 3 (step S7). Then, the control unit 2 stores the acquired pulse rate and maximum pulse rate in the storage unit 5 in association with the acquired ID (step S8).

To the display unit 6, the information output unit 23 of the exercise information measurement apparatus 10-1 outputs information for displaying icons corresponding to the respective IDs of the exercise information measurement apparatuses 10-1 to 10-5 stored in the storage unit 5. Based on this information, the display unit 6 displays icons that are color-coded according to the pulse rates and the maximum pulse rates corresponding to the respective IDs of the exercise information measurement apparatuses 10-1 to 10-5 (step S9).

Specifically, on the display unit 6, the information output unit 23 displays icons that are color-coded according to the sizes of values (hereinafter referred to as "exercise load percentages") obtained by dividing the pulse rates corresponding to the IDs of the exercise information measurement apparatuses 10-1 to 10-5 by the maximum pulse rates corresponding to those IDs. In the present embodiment, an icon is displayed with a lighter color the smaller the exercise load percentage is.

Also, based on the pulse rates corresponding to the respective IDs of the exercise information measurement apparatuses 10-1 to 10-5, the information output unit 23 of the exercise information measurement apparatus 10-1 generates management information for managing the actions of all of the group members belonging to the group composed of the exercise information measurement apparatuses 10-1 to 10-5 and outputs the generated management information to the display unit 6 (step S10). After step S10, the processing returns to step S2a.

Examples of methods for generating management information include the following three methods.

First Method for Generating Management Information

The information output unit 23 calculates the average value of the exercise load percentages (a total of five exercise load percentages) calculated for the respective IDs of the exercise information measurement apparatuses 10-1 to 10-5, and generates information indicating the exercise load of the entire group as the management information in accordance with the size of the calculated average value.

For example, if the average value of the five exercise load percentages is greater than or equal to a threshold value TH1 (the threshold value TH1 being a value less than 1), the information output unit 23 determines that the exercise load of the entire group constituted by users A to E is high, and generates information indicating that the exercise load of the entire group is high as first management information.

If the average value is less than the threshold value TH1, the information output unit 23 generates information indicating that the exercise load of the entire group is appropriate as second management information. Here, the average value is compared with only the threshold value TH1, but it is also possible to provide multiple threshold values and generate management information with different content according to the size of the average value. Also, the threshold value TH1 may be set arbitrarily according to the purpose of the group action.

Second Method for Generating Management Information

Among the exercise load percentages (a total of five exercise load percentages) calculated for the respective IDs of the exercise information measurement apparatuses 10-1 to 10-5, the information output unit 23 selects multiple (a number that is less than the total number of apparatuses constituting the group) upper-level exercise load percentages with large values and calculates the average value of the multiple selected exercise load percentages. Also, the information output unit 23 generates information indicating the exercise load of the entire group as the management information, in accordance with the size of the calculated average value. Specific examples of information indicating the exercise load of the entire group are the same as those described in the first method for generating management information.

Third Method for Generating Management Information

If, among the exercise load percentages calculated for the respective IDs of the exercise information measurement apparatuses 10-1 to 10-5, the number of IDs with exercise load percentages that exceed a threshold value TH2 (threshold value TH2 being a value less than 1; for example, 0.8) exceeds a predetermined value (e.g., 70% of the number of members constituting the group), the information output unit 23 generates information indicating that the exercise load of the entire group is high as the first management information.

Also, if, among the exercise load percentages calculated for the respective IDs of the exercise information measurement apparatuses 10-1 to 10-5, the number of IDs with exercise load percentages that exceed the threshold value TH2 is less than or equal to the predetermined value, the information output unit 23 generates information indicating that the exercise load of the entire group is appropriate as the second management information. Thus, the information output unit 23 generates information indicating the exercise load of the entire group as the management information in accordance with the number of users with exercise load percentages that exceed the threshold value TH2.

Figure 5:
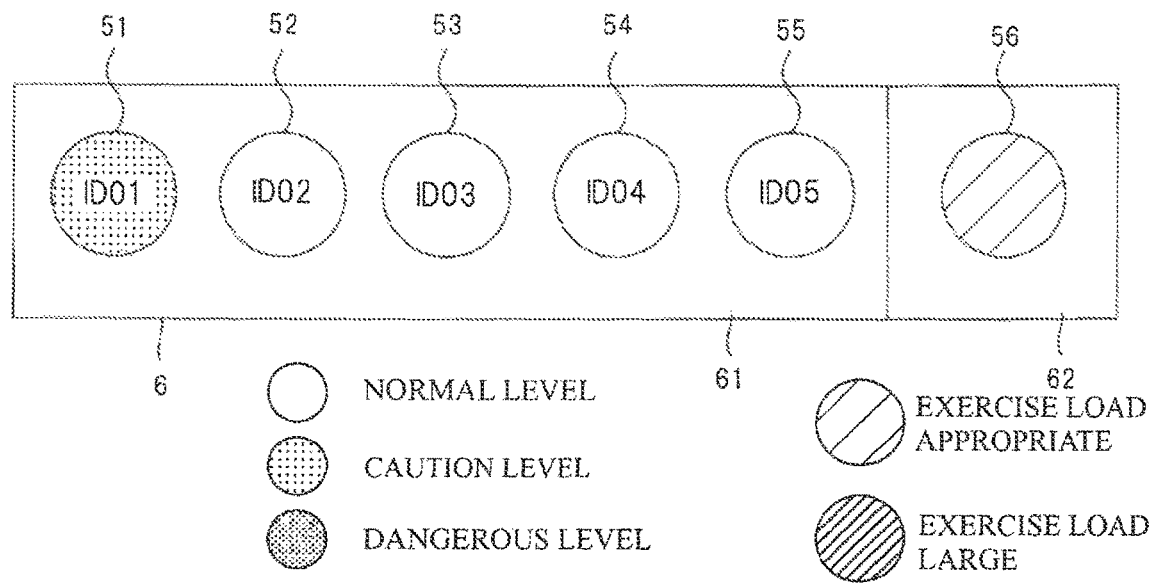
FIG. 5 is a diagram showing an example of a first screen displayed on a display unit 6 of the exercise information measurement apparatus 10 set as a master device.

FIG. 5 is a diagram showing an example of a screen displayed on the display unit 6 of the exercise information measurement apparatus 10-1 set as the master device as a result of steps S9 and S10 of FIG. 4.

As shown in FIG. 5, the screen displayed on the display unit 6 includes a member state display region 61 and a management information display region 62.

The member state display region 61 is a region in which icons 51 to 55 that correspond to the respective IDs of the exercise information measurement apparatuses 10-1 to 10-5 are displayed. The icon 51 in which ID:01 is written is the icon corresponding to the exercise information measurement apparatus 10-1. The icon 52 in which ID:02 is written is the icon corresponding to the exercise information measurement apparatus 10-2. The icon 53 in which ID:03 is written is the icon corresponding to the exercise information measurement apparatus 10-3. The icon 54 in which ID:04 is written is the icon corresponding to the exercise information measurement apparatus 10-4. The icon 55 in which ID:05 is written is the icon corresponding to the exercise information measurement apparatus 10-5.

In the present embodiment, an icon with an exercise load percentage of less than 0.5 is indicated as a white circle, which indicates a normal level. An icon with an exercise load percentage that is 0.5 or more and less than 0.9 is indicated as a circle with a low-density dot pattern, which indicates a caution level. An icon with an exercise load percentage that is 0.9 or more is indicated as a circle with a high-density dot pattern, which indicates a dangerous level.

In the example shown in FIG. 5, it can be understood that only the exercise load percentage of the wearer of the exercise information measurement apparatus 10-1 is at the caution level, and the exercise load percentages of the wearers of the other exercise information measurement apparatuses 10-2 to 10-5 are at the normal level.

The management information display region 62 is a region in which the icon 56 based on the management information output by the information output unit 23 is displayed.

In the present embodiment, the icon based on the first management information is indicated as a circle with diagonal hatching having a small diagonal line interval, which indicates that the exercise load is large. Also, the icon based on the second management information is indicated as a circle with diagonal hatching having a large diagonal line interval, which indicates that the exercise load is appropriate.

In the example shown in FIG. 5, an icon 56 indicating that the exercise load for the entire group is appropriate is displayed in the management information display region 62.

By viewing the screen shown in FIG. 5, user A can instantly find out the states of the respective exercise loads of the members belonging to the group, and can instantly find out whether or not the exercise load of the entire group is appropriate with the icon 56.

Figure 6:
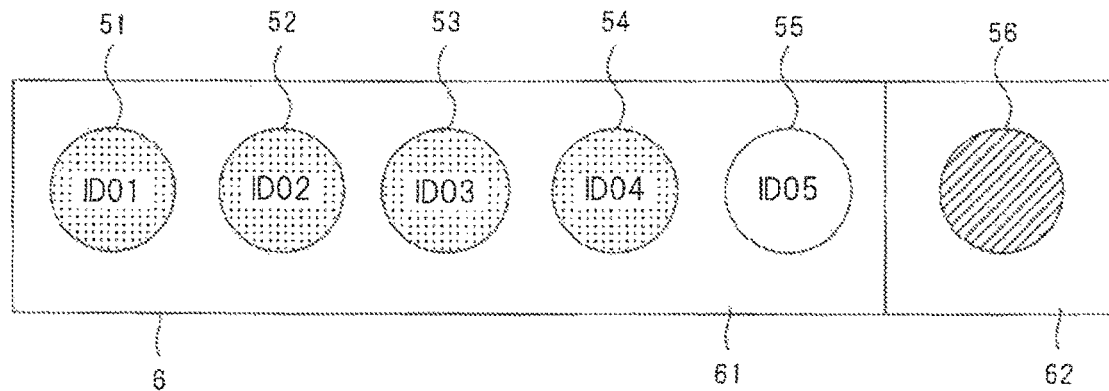
FIG. 6 is a diagram showing an example of a second screen displayed on the display unit 6 of the exercise information measurement apparatus 10 set as the master device.

For example, if the screen shown in FIG. 5 is displayed on the display unit 6, the exercise load is appropriate for the group, and therefore the leader does not need to do anything in particular. On the other hand, if the screen shown in FIG. 6 is displayed on the display unit 6, the user A determines that the exercise load is high for the group and verbally instructs the group members to take a break, or verbally instructs the group members to reduce their movement pace. Thus, with the screen shown in FIG. 6, the exercise load of the entire group can be appropriately managed.

Although a case in which mountain climbing is performed in a group was given as an example here, there is no limitation to mountain climbing, and it is possible to manage a group action using the exercise information measurement apparatus 10 in various scenes, such as a case of performing walking in a group, a case of performing running in a group, and a case of performing a tour by bicycle in a group.

According to the exercise information measurement apparatus 10, there is a possibility that the icon 56 shown in FIG. 6 will be displayed even if none of the respective exercise load percentages of users A to E have reached the dangerous level. For this reason, care can be given at a stage before the body of a group member enters a dangerous state, and it is possible to prevent an accident during a group action.

According to the exercise information measurement apparatus 10, bodily information is exchanged via the communication unit 3, management information is generated based on the bodily information of the group members, and the generated management information is output. For this reason, it is possible to manage a group action even in a location with no infrastructure for connecting to a network such as the Internet, whereby convenience can be increased. Also, since near-field wireless communication can be carried out with low power consumption, it is possible to extend the battery life of the exercise information measurement apparatus 10.

In the operation example of FIG. 4, the information output unit 23 of the exercise information measurement apparatus 10-1 displays the icons 51 to 55 on the display unit 6, but it is also possible to use a configuration in which only the icon 56 is displayed on the display unit 6.

For example, it is conceivable that all elementary school students on an elementary school field trip perform movement wearing exercise information measurement apparatuses 10. In this case, it is not practical for a teacher to perform pulse rate management for each individual student. If the icon 56 is displayed on the display unit 6, it is at least possible to determine whether or not the exercise load is appropriate for the group and to broadly manage the group action. For this reason, it is not essential that the member state display region 61 is displayed.

With the exercise information measurement apparatus 10, a configuration is possible in which an icon displayed on the display unit 6 can be selected using the operation unit 4. Then, if an icon has been selected through operation of the operation unit 4, the control unit 2 may transmit instruction information to the exercise information measurement apparatus 10 corresponding to the selected icon.

For example, if the icon 56 is selected by user A on the screen shown in FIG. 6, the control unit 2 of the exercise information measurement apparatus 10-1 transmits instruction information for giving an instruction to reduce the exercise load to all of the exercise information measurement apparatuses 10 belonging to the group, via the communication unit 3.

In the exercise information measurement apparatus 10 that has received the instruction information, the control unit 2 reads out message data corresponding to the instruction information from the storage unit 5 and displays the read-out message data on the display unit 6. Accordingly, for example, messages such as "Let's take a break" or "Please reduce your pace" are shown on the display unit 6.

With this configuration, even if user A and the other users B to E are separated, it is possible for user A to give an appropriate instruction to the other users B to E through a remote operation.

Also, for example, if an icon displayed in the member state display region 61 indicates a dangerous level, when the icon is selected by user A, the control unit 2 of the exercise information measurement apparatus 10-1 transmits instruction information for giving an instruction to reduce the exercise load to the exercise information measurement apparatus 10 corresponding to the selected icon.

In the exercise information measurement apparatus 10 that has received the instruction information, the control unit 2 reads out message data (data such as a message giving an instruction to take a break or a message giving an instruction to reduce the pace) corresponding to the instruction information from the storage unit 5 and displays the read-out message data on the display unit 6. With this kind of configuration, it is also possible to individually manage the actions of members of the group.

In the description above, the screens shown in FIGS. 5 and 6 are displayed only on the exercise information measurement apparatus 10-1 set as the master device. As a modified example of this, it is possible to display the screens shown in FIGS. 5 and 6 on the exercise information measurement apparatuses 10 constituting the group.

For example, the information output unit 23 of the exercise information measurement apparatus 10-1 generates display data for displaying the screen shown in FIG. 5 or 6, and thereafter transmits the display data to the exercise information measurement apparatuses 10 belonging to the group via the communication unit 3. The control unit 2 of an exercise information measurement apparatus 10 that has received the display data outputs the display data to the display unit 6. Then, the screen shown in FIG. 5 or 6 is displayed on the display unit 6 of a slave device as well.

By doing so, all of the group members can keep track of the bodily states of the members and the exercise load of the entire group. As a result, the members can perform actions while being aware of the entire group, which increases the quality of the group action.

In the description above, the information output unit 23 of the exercise information measurement apparatus 10-1 set as the master device outputs management information for managing the actions of all group members. As a modified example of this, it is also possible to use a configuration in which the information output unit 23 outputs management information for managing the action of a specific member in the group.

Figure 7:
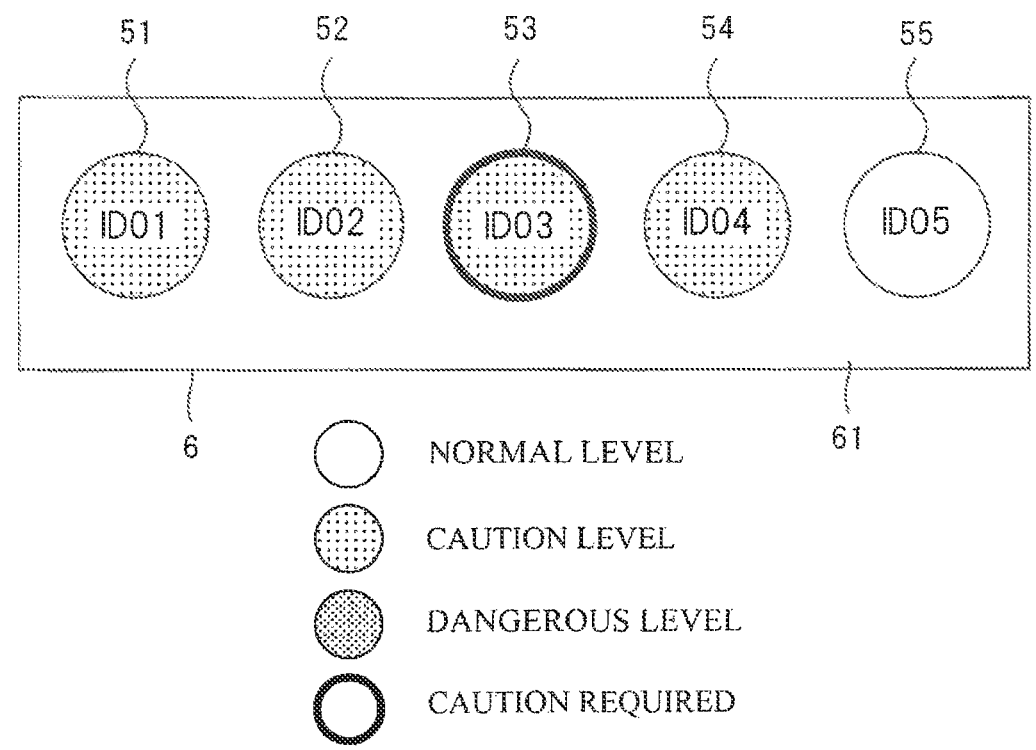
FIG. 7 is a diagram showing an example of a third screen displayed on the display unit 6 of the exercise information measurement apparatus 10 set as the master device.

FIG. 7 is a diagram showing a display example of a screen based on management information generated by the information output unit 23. In the example shown in FIG. 7, only the member state display region 61 illustrated in FIG. 5 is displayed on the display unit 6. Also, only the icon 53 is subjected to highlighted display due to being surrounded by a thick black line.

The information output unit 23 generates information for performing highlighted display as the management information and outputs the management information to the display unit 6.

For example, the information output unit 23 specifies the ID whose corresponding exercise load is the largest among the IDs of the exercise information measurement apparatuses 10-1 to 10-5, and generates information for performing notification of the wearer of the exercise information measurement apparatus 10 indicated by the specified ID as the management information.

In the example shown in FIG. 7, in order to indicate that caution is to be given to the action of the wearer of the exercise information measurement apparatus 10-3 indicated by ID:03, whose exercise load percentage is the largest, the information output unit 23 outputs information for highlighting the icon 53 corresponding to the ID:03 as the management information to the display unit 6. Accordingly, the icon 53 displayed on the display unit 6 is highlighted.

By looking at the screen shown in FIG. 7, user A can find out that user C of the exercise information measurement apparatus 10-3 has a higher exercise load compared to the other users. For this reason, user A can give user C an instruction to take a rest or reduce the pace.

Thus, by specifying a user whose exercise load (exercise load percentage) is the largest based on the pulse rates of the users belonging to a group and subjecting the icon corresponding to that user to highlighted display, it is possible to perform notification of the status of the exercise load using a member of the group as a reference.

Caution is prompted not by performing notification if the exercise load of an individual is at a dangerous level, but by performing notification of a member whose exercise load is higher compared to the exercise loads of the members of the group. By doing so, it is possible to keep track of members who require caution although they have not reached the dangerous level while a group action is in progress, and suitable management of the group action is possible.

Note that the information output unit 23 may calculate an average value of exercise load percentages corresponding to the respective IDs of the exercise information measurement apparatuses 10-1 to 10-5, specify an ID for which a value obtained by subtracting the average value from the exercise load percentage of the corresponding apparatus exceeds a threshold value, generate information for performing notification of the wearer of the exercise information measurement apparatus 10 indicated by the specified ID as management information, and output the information. With this configuration as well, through highlighted display based on the management information, it is possible to keep track of a user whose exercise load is higher compared to the other users in the group and who requires caution.

Note that the information output unit 23 may calculate change percentages per unit time of exercise load percentages corresponding to the respective IDs of the exercise information measurement apparatuses 10-1 to 10-5, specify an ID for which a difference between the change percentage and an average value of the change percentages calculated for the apparatuses exceeds a threshold value, generate information for performing notification of the wearer of the exercise information measurement apparatus 10 indicated by the specified ID as management information, and output the information.

For example, it is assumed that the five-minute pulse rate change percentage of the wearers of the exercise information measurement apparatuses 10-1, 10-2, 10-4, and 10-5 is 10%, and the five-minute pulse rate change percentage of the wearer of the exercise information measurement apparatus 10-3 is 40%. If the threshold is 10%, the wearer for which the difference between the change percentage and the average value (=16%) of the change percentages of the exercise load percentages of all of the users in the group exceeds 10% is user C of the exercise information measurement apparatus 10-3. Accordingly, as shown in FIG. 7, the icon 53 corresponding to the exercise information measurement apparatus 10-3 worn by the user C is subjected to highlighted display.

In the case of performing a group action, the members of the group perform the same action, and therefore the change percentages of the exercise load percentages should have similar trends. Accordingly, if there is a member for whom the difference between the change percentage of the exercise load percentage and the average value of the change percentages of all members exceeds the threshold value, it can be determined that the exercise load of this member is too high. In view of this, by subjecting the icon corresponding to that member to highlighted display, it is possible to notify the leader that care is needed for that member, and suitable management of the group action is possible.

There is a possibility that the highlighted display shown in FIG. 7 will be performed even if the exercise load percentage of user C has not reached the dangerous level. For this reason, it is possible to give care at a stage prior to the body of the user C entering a dangerous state, and it is possible to prevent an accident during a group action.

Note that the pulse sensor 7 shown in FIG. 2 need only function as a bodily information measurement unit that measures bodily information indicating the exercise load of the wearer of the apparatus, and is not limited to being a pulse sensor. For example, it is also possible to use a heartbeat sensor or a sensor that measures an oxygen saturation.

A program for causing a computer to execute the steps of the flowchart shown in FIG. 4 or a program for causing a computer to function as the functional blocks shown in FIG. 2 can be provided by a program being recorded on a computer-readable non-transitory recording medium.

Examples of this kind of "computer-readable recording medium" include an optical medium such as a CD-ROM (Compact Disc-ROM), a magnetic recording medium such as a memory card, and the like. Also, this kind of program can be provided by downloading via a network.

In the description above, setting of the master device and the slave devices is performed by the exercise information measurement apparatuses 10, but the method for group creation is not limited thereto, and a known method can be used. For example, a list of certain other apparatuses 10 in a range in which communication with an exercise information measurement apparatus 10 set as the master device is possible may be displayed on the display unit 6 of the master device, and the wearer of the master device may select a device to be set as a member from among the displayed other apparatuses so as to set the selected other apparatus 10 as a slave device.

The embodiment disclosed herein is to be thought of as being in all ways exemplary and in no ways limiting. The scope of the present invention is indicated by the claims and not by the above-described embodiment, and equivalent meanings as well as all modifications that fall within the scope are intended to be included in the scope of the invention.

As described above, the following items are disclosed in the present specification.

The disclosed action management apparatus includes: a bodily information measurement unit configured to measure bodily information; a communication unit for performing near-field wireless communication with another apparatus having a function of measuring bodily information; a bodily information acquisition unit configured to, via the communication unit, acquire bodily information measured by another apparatus included in a group along with the action management apparatus; and an information output unit configured to, based on first bodily information measured by the bodily information measurement unit and second bodily information acquired by the bodily information acquisition unit, output management information for managing an action of a wearer of an apparatus belonging to the group.

With the disclosed action management apparatus, as the management information, the information output unit outputs information for managing actions of wearers of all apparatuses belonging to the group.

With the disclosed action management apparatus, the information output unit calculates an average value of some or all exercise loads of the wearers of all of the apparatuses obtained based on the first bodily information and the second bodily information, and in accordance with a size of the average value, generates information indicating an exercise load of the entire group constituted by the wearers of all of the apparatuses, and outputs the information as the management information.

With the disclosed action management apparatus, the information output unit determines the number of exercise loads that exceed a threshold value among exercise loads obtained based on the first bodily information and the second bodily information, and in accordance with the number, generates information indicating an exercise load of the entire group constituted by the wearers of all of the apparatuses, and outputs the information as the management information.

With the disclosed action management apparatus, based on the first bodily information and the second bodily information, the information output unit specifies an apparatus for which an exercise load of a wearer is the largest among all apparatuses constituting the group, and outputs information for performing notification of the wearer of the specified apparatus as the management information.

With the disclosed action management apparatus, based on the first bodily information and the second bodily information, the information output unit calculates an average value of exercise loads of wearers of all apparatuses constituting the group, specifies a wearer for whom a value obtained by subtracting the average value from the exercise load of the wearer exceeds a threshold value, and outputs information for performing notification of the specified wearer as the management information.

With the disclosed action management apparatus, based on the first bodily information and the second bodily information, the information output unit calculates change percentages of exercise loads of wearers of all apparatuses constituting the group, specifies a wearer for whom a difference between the change percentage and an average value of the change percentages calculated for all of the apparatuses exceeds a threshold value, and outputs information for performing notification of the specified wearer as the management information.

The disclosed action management method is An action management method performed by an action management apparatus including a bodily information measurement unit configured to measure bodily information, and a communication unit for performing near-field wireless communication with another apparatus having a function of measuring bodily information, the method including: a bodily information acquisition step of, via the communication unit, acquiring bodily information measured by another apparatus included in a group along with the action management apparatus; and an information output step of, based on first bodily information measured by the bodily information measurement unit and second bodily information acquired in the bodily information acquisition step, outputting management information for managing an action of a wearer of an apparatus belonging to the group.

The disclosed action management program is a program for causing a computer to execute the steps of the action management method.

INDUSTRIAL APPLICABILITY

According to the present invention, it is possible to provide an action management apparatus, an action management method, and an action management program according to which it is possible to suitably manage a group action.

While the present invention has been described with reference to specific embodiments, the present invention is not limited to these embodiments, and many variations and modifications can be made without departing from the technical idea of the disclosed invention. The present application claims the benefit of Japanese Patent Application 2014-245929 filed on Dec. 4, 2014, which is hereby incorporated herein in its entirety.

REFERENCE SIGNS LIST

2 Control unit
3 Communication unit
6 Display unit
10, 10-1 to 10-5 Exercise information measurement apparatus
20 Bodily information measurement unit
22 Bodily information acquisition unit
23 Information output unit

The invention claimed is:

1. A system comprising:
a first action management apparatus configured to be carried by a first user and a second action management apparatus configured to be carried by a second user, the first action management apparatus having a same circuit structure as a circuit structure of the second action management apparatus,
the first action management apparatus including:
a first communication unit configured to perform near-field wireless communication with the second action management apparatus; and
a first controller configured to:
set the first action management apparatus as either a master device or a slave device;
receive a measured maximum pulse rate of the first user; and
in response to the first action management apparatus being set as the slave device, transmit the received maximum pulse rate of the first user from the first action management apparatus to the second action management apparatus via the first communication unit; and
the second action management apparatus including:
a second communication unit configured to perform near-field wireless communication with the first action management apparatus; and
a second controller configured to:
set the second action management apparatus as either one of a master device of a slave device;
received a maximum pulse rate of the second user;
in response to the second action management apparatus being set as the master device, and based on the received maximum pulse rate of the second user and the maximum pulse rate of the first user:
calculate respective exercise load percentages of the first and second users based on the maximum pulse rates of the first user and the second user, respectively;
calculate an average of the exercise load percentages of the first user and the second user;
generate a first icon, a second icon, and a third icon representing the exercise load percentage of the second user, the exercise load percentage of the first user, and the calculated average of the exercise load percentages of the first user and the second user, respectively, and
output the first icon, the second icon, and the third icon on a display of the second action management apparatus.

2. A system comprising:
a first action management apparatus configured to be carried by a first user and a second action management apparatus configured to be carried by a second user, the first action management apparatus having a same circuit structure as a circuit structure of the second action management apparatus,
the first action management apparatus including:
a first communication unit configured to perform near-field wireless communication with the second action management apparatus; and
a first controller configured to:
set the first action management apparatus as either a master device or a slave device;
receive a maximum pulse rate of the first user; and
in response to the first action management apparatus being set as the slave device, transmit the received maximum pulse rate of the first user from the first action management apparatus to the second action management apparatus via the first communication unit; and
the second action management apparatus including:
a second communication unit configured to perform near-field wireless communication with the first action management apparatus; and
a second controller configured to:
set the second action management apparatus as either one of a master device of a slave device;
receive a maximum pulse rate of the second user; and
in response to the second action management apparatus being set as the master device, and based on the received maximum pulse rate of the second user and an acquired maximum pulse rate of the first user:
calculate respective exercise load percentages of the first and second users based on the maximum pulse rates of the first user and the second user, respectively;
calculate a change percentage for each of the exercise load percentages of the first user and the second user, the change percentage of the first user being equal to a change in the exercise load percentage of the first user per a unit of time, and the change percentage of the second user being equal to a change in the exercise load percentage of the second user per the unit of time;
calculate an average change percentage based on the change percentage of the first user and the change percentage of the second user;
generate a first icon, a second icon, and a third icon representing the exercise load percentage of the second user, the exercise load percentage of the first user, and a calculated average change percentage, respectively; and
output the first icon, the second icon, and the third icon on a display of the second action management apparatus.

3. An action management method performed by a first action management apparatus and a second action management apparatus, the first action management apparatus and the second action management apparatus being configured to be carried by a first user and a second user, respectively, and the first action management apparatus having a same circuit structure as a circuit structure of the second action management apparatus, the action management method comprising:
setting the second action management apparatus as a master device;
setting the first action management apparatus as a slave device;
receiving a maximum pulse rate of the first user with the first action management apparatus;
receiving a maximum pulse rate of the second user with the second action management apparatus;
transmitting the received maximum pulse rate of the first user from the first action management apparatus to the second action management apparatus by performing near-field wireless communication via the first communication unit;
calculate respective exercise load percentages of the first and second users based on the maximum pulse rate of the first user and an acquired maximum pulse rate of the second user, respectively;
calculate an average of the exercise load percentages of the first user and the second user;
generating a first icon, a second icon, and a third icon representing the exercise load percentage of the first user, the exercise load percentage of the second user, and the calculated average of the exercise load percentages, respectively;
outputting the first icon, the second icon, and the third icon on a display of the first action management apparatus; and
based on the received maximum pulse rate of the second user and an acquired maximum pulse rate of the first user:
calculating respective exercise load percentages of the first and second users based on the maximum pulse rates of the first user and the second user, respectively;
calculating an average of the exercise load percentages of the first user and the second user;
generating a first icon, a second icon, and a third icon representing the exercise load percentage of the second user, the exercise load percentage of the first user, and the calculated average of the exercise load percentages of the first user and the second user, respectively; and
outputting the first icon, the second icon, and the third icon on a display of the second action management apparatus.

4. An action management method performed by a first action management apparatus and a second action management apparatus, the first action management apparatus and the second action management apparatus being configured to be carried by a first user and a second user, respectively, and the first action management apparatus having a same circuit structure as a circuit structure of the second action management apparatus, the action management method comprising:

setting the second action management apparatus as a master device;

setting the first action management apparatus as a slave device;

receiving a maximum pulse rate of the first user with the first action management apparatus;

receiving a maximum pulse rate of the second user with the second action management apparatus;

transmitting the received maximum pulse rate of the first user from the first action management apparatus to the second action management apparatus by performing near-field wireless communication via the first communication unit;

calculate respective exercise load percentages of the first and second users based on the maximum pulse rate of the first user and an acquired maximum pulse rate of the second user, respectively;

generating a first icon, a second icon, and a third icon representing the received exercise load percentage of the first user, the acquired exercise load percentage of the second user, and the calculated average of the exercise load percentages, respectively;

outputting the first icon, the second icon, and the third icon on a display of the first action management apparatus; and based on the received maximum pulse rate of the second user and an acquired maximum pulse rate of the first user:

calculating respective exercise load percentages of the first and second users based on the maximum pulse rates of the first user and the second user, respectively;

calculating a change percentage for each of the exercise load percentages of the first user and the second user, the change percentage of the first user being equal to a change in the exercise load percentage of the first user per a unit of time, and the change percentage of the second user being equal to a change in the exercise load percentage of the second user per the unit of time;

calculate an average change percentage based on the change percentage of the first user and the change percentage of the second user;

generating a first icon, a second icon, and a third icon representing the exercise load percentage of the second user, the exercise load percentage bodily information of the first user, and the calculated average change percentage, respectively; and outputting the first icon, the second icon, and the third icon on a display of the second action management apparatus.

5. A non-transitory computer readable storage medium storing an action management program causing a computer to execute the steps of the action management method according to claim 3.

* * * * *